(12) United States Patent
Beumer

(10) Patent No.: US 8,846,961 B2
(45) Date of Patent: Sep. 30, 2014

(54) SYNTHESIS OF PERETINOIN

(75) Inventor: Raphael Beumer, Basel (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/877,211

(22) PCT Filed: Sep. 29, 2011

(86) PCT No.: PCT/EP2011/066963
§ 371 (c)(1),
(2), (4) Date: Jun. 10, 2013

(87) PCT Pub. No.: WO2012/041948
PCT Pub. Date: Apr. 5, 2012

(65) Prior Publication Data
US 2013/0310586 A1    Nov. 21, 2013

(30) Foreign Application Priority Data

Oct. 1, 2010  (EP) .................................... 10185735

(51) Int. Cl.
*C07B 33/00*    (2006.01)
*C07C 51/16*    (2006.01)
*C07C 45/51*    (2006.01)
*C07C 253/30*   (2006.01)

(52) U.S. Cl.
CPC ............... *C07C 51/16* (2013.01); *C07C 45/513* (2013.01); *C07C 253/30* (2013.01)
USPC ........................................................ 554/132

(58) Field of Classification Search
CPC .... C07C 67/03; C07C 67/333; C07C 53/126; C07C 51/245; C08I 91/10
USPC .......................................................... 554/132
See application file for complete search history.

(56) References Cited

U.S. PATENT DOCUMENTS 3,029,287 A    4/1962  Roman et al.
6,184,420 B1   2/2001  Teles et al.

FOREIGN PATENT DOCUMENTS

CN    1 817 841         8/2006
CN    1817841      *   8/2006

OTHER PUBLICATIONS

International Search Report for PCT/EP2011/066963 mailed Nov. 30, 2011.
G. Saucy et al., "Über Eine Neuartige Synthesis von Beta-Ketoallenen Durch Reacktion von Tertiären Acetylencarbinolen Mit Vinyläthern", Helvetica Chimica Acta., vol. 50, No. 119, Jan. 1, 1967, pp. 1158-1167.

* cited by examiner

*Primary Examiner* — Deborah D Carr
(74) *Attorney, Agent, or Firm* — Nixon & Vanderhye P.C.

(57) ABSTRACT

The present invention relates to a new and improved synthesis of peretinoin.

3 Claims, No Drawings

SYNTHESIS OF PERETINOIN

This application is the U.S. national phase of International Application No. PCT/EP2011/066963 filed 29 Sep. 2011 which designated the U.S. and claims priority to EP 10185735.7 filed 1 Oct. 2010, the entire contents of each of which are hereby incorporated by reference.

The present invention relates to a new and improved synthesis of peretinoin.

Peretinoin (also known as NIK 333) is an acyclic retinoid. This compound is useful in reducing the recurrence of hepatocellular carcinoma (HCC) after surgical resection or ablation in hepatitis C virus (HCV) positive patients.

Liver cancer is the sixth most common cancer in the world, and more than six hundred thousand patients are newly diagnosed every year. In Japan, liver cancer is the third leading cause of death from cancer. The newly diagnosed patients are about 40,000, and about 35,000 patients die every year. Primary liver cancer is classified into HCC and cholangiocellular carcinoma, and about 94% is HCC. HCC are mainly caused by the infections of hepatitis B virus or HCV, and in Japan about 67% of HCC are caused by the HCV. HCV positive HCC is known to have a high recurrence rate after curative resection, and the recurrence rates are 24%, 76%, 92% within 1, 3, 5 years, respectively.

Peretinoin is an important compound in the fight against liver cancer. Therefore any improved way to synthesise this compound is important.

The present invention relates to an improved process of production of peretinoin, wherein this process comprises a step in which dehydronerolidol is reacted with 2-alkoxypropene without a solvent.

Therefore the process of production of peretinoin is characterised in that it comprises the following reaction step a), wherein
a compound of formula (I) (known as dehydronerolidol (EDNL))

(I)

is reacted with a compound of formula (II)

(II)

wherein R is a $C_1$-$C_4$ alkyl group, characterized in that this reaction is carried out without a solvent.

The reaction of step a) is done with out using a solvent. The yields of the obtained compound of formula (III)

(III)

are good.

Not using a solvent (but only a slight excess of compound (II)) has the advantages that
(i) the isolation and purification of product (III) is easier (no solvent has to be removed) and that
(ii) there is no need to handle a solvent (an additional source of impurities, etc).

After the step a) the reaction product of step a), which is the compound of formula (III), (III)

is reacted with a compound of formula (IV)

(IV)

wherein $R_1$ is H or a $C_1$-$C_4$ alkyl group. It is also possible that the $COOR_1$ group can be in the form of a salt. The cation is not critical for the reaction. Suitable cations are i.e. alkali metals or ammonium.

Afterwards the reaction product of step b) (compound of formula (V))

(V)

is saponified to a compound of formula (VI) in step c).

The product obtainable by the reaction of step c) is NIK 333 (compound of formula (VI), wherein $R_1$ is H).

(VI)

Alternatively the compound of formula (VI) can be obtained directly from compound of formula (III) by reacting the compound of formula (III) with the reaction product of step a) with a Wittig reagent derived from a compound of formula (VII)

$$Y\text{—}CH_2\text{—}CO_2R_1 \quad (VII)$$

wherein Y is a halogen atom and $R_1$ is H or a $C_1$-$C_4$-alkyl group.

In the context of this invention this step is defined as step d).

Such a reaction can i.e. be found in US 49917829 (process A in column 1).

In the following each reaction step a) to d) are discussed in more details.

Step a)

Dehydronerolidol (EDNL)]

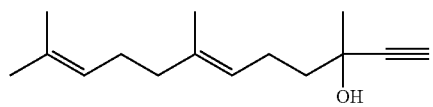

is reacted with a compound of formula (II)

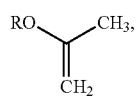

wherein R is a $C_1$-$C_4$ alkyl group.

The reaction is carried out in the presence of a catalytic amount of sulfuric acid. Preferably, the reaction temperature is between 100° C. and 130° C., more preferably between 105° C. and 120° C.

Usually the reaction is carried out under pressure. Usually more than 4 bar are used. Preferably more than 6 bar, more preferably the pressure is about 6 bar. Compound (II) is added in excess in comparison to compound (I).

Preferably a compound of formula (IIa)

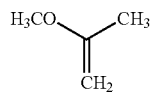

is used.

The isolation of compound (III) is done by using commonly known processes.

Step b)

The reaction product of step a), which is the compound of formula (III)

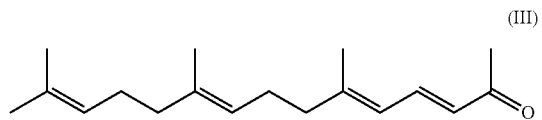 [SMILES: CC(=O)/C=C/C=C(\C)CC/C=C(\C)CCC=C(C)C]

is reacted with a compound of formula (IV)

wherein $R_1$ is H or a $C_1$-$C_4$ alkyl group.

It is also possible that the $COOR_1$ group can be in the form of a salt. The cation is not critical for the reaction. Suitable cations are i.e. alkali metals or ammonium.

This reaction can be done by using commonly known process conditions. The reaction is preferably catalysed by pyridine and ammonium acetate. As a solvent, toluene can be used. The reaction mixture is stirred under reflux at elevated temperatures. The reaction product (compound of formula (V))

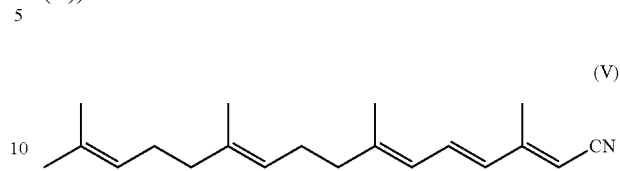

is obtained. The isolation of the compound of formula (V) is carried out by using commonly known processes.

Step c)

The reaction production of step b) is saponified into the compound of formula (VI). Processes of this type are known from the prior art. Such a reaction is i.e. disclosed in J. Am. Chem. Soc., 1984, 106, 7890-7893. This document is hereby incorporated by reference.

The reactions steps are disclosed in details on page 7893 of this publication. First the reduction of the nitrile to aldehyde is carried out, afterwards the oxidation of this aldehyde to the methylester.

Step d)

Alternatively the compound of formula (VI) can be obtained directly by a process wherein the reaction product of step a) is reacted with a Wittig reagent derived from a compound of formula (VII)

$$Y—CH_2—CO_2R_1 \qquad (VII)$$

wherein Y is a halogen atom and $R_1$ is H or a $C_1$-$C_4$-alkyl group.

Such a reaction can i.e. be found in U.S 49917829 (process A in column 1). This document is hereby incorporated by reference.

Examples of the Wittig reagents employed in the above-described reaction and derived from a compound of the general formula (VII) include phosphoric compounds produced by the reaction between the compound of the general formula (VII) and triphenylphosphine, phenyldialkoxyphosphine, trialkylphosphite, or the like. The preparation of the reagent and the Wittig reaction employing the reagent are carried out by the conventional methods such as the method given by Wadworth, et al. in J. Am. Chem. Soc., vol. 83, p. 1733 (1961), the method given by Greenwald, et al. in J. Org. Chem., vol. 28, p. 1128 (1963), and the method given by Homer, et al. in Ber. vol. 95, p. 581 (1962).

The invention claimed is:

1. A process for the production of peretinoin comprising the following reaction steps:

a) reacting a compound of formula (I) without using a solvent,

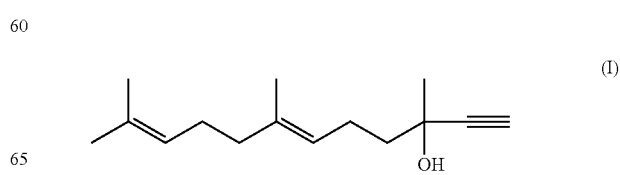

with a compound of formula (II),

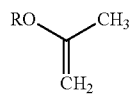
(II)

wherein R is a $C_1$-$C_4$ alkyl group, to thereby obtain a reaction product which is a compound of formula (III),

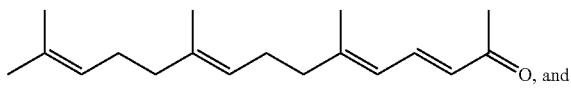
(III)

b) reacting the reaction product of formula (III) obtained in step a) with a compound of formula (IV)

(IV)

wherein R1 is H, a $C_1$-$C_4$ alkyl group and salts thereof.

2. The process according to claim 1, wherein the reaction product of step b) is a compound of formula (V)

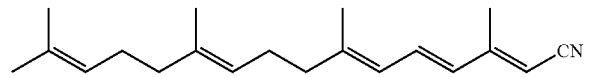
(V)

and wherein the process further comprises the step of:
c) saponifying the compound of formula (V) to a compound of formula (VI)

(VI)

wherein $R_1$ is H or a $C_1$-$C_4$ alkyl group.

3. A process for the production of peretinoin comprising the following reaction steps:
a) reacting a compound of formula (I) without using a solvent,

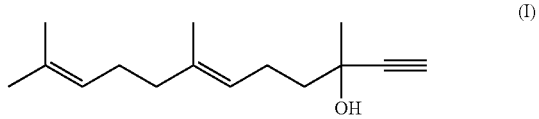 [SMILES: C#CC(C)(O)CC/C=C(\C)CCC=C(C)C]
(I)

with a compound of formula (II)

(II)

wherein R is a $C_1$-$C_4$ alkyl group, and
b) reacting the reaction product of step a) with a Wittig reagent derived from a compound of formula (VII)

Y—$CH_2$—$CO_2R_1$ (VII)

wherein Y is a halogen atom and $R_1$ is H or a $C_1$-$C_4$ alkyl group.

* * * * *